(12) United States Patent
Diges et al.

(10) Patent No.: US 8,357,672 B2
(45) Date of Patent: Jan. 22, 2013

(54) CELL LYSIS REAGENT FOR ISOLATION OF RNA

(75) Inventors: Camille M. Diges, Oakland, CA (US); Luis Ugozzoli, San Rafael, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 360 days.

(21) Appl. No.: 12/479,484

(22) Filed: Jun. 5, 2009

(65) Prior Publication Data

US 2009/0317894 A1   Dec. 24, 2009

Related U.S. Application Data

(60) Provisional application No. 61/061,159, filed on Jun. 13, 2008.

(51) Int. Cl.
*A61K 31/727* (2006.01)

(52) U.S. Cl. .......................................................... 514/56

(58) Field of Classification Search .................... 514/56; 435/270

See application file for complete search history.

(56) References Cited

U.S. PATENT DOCUMENTS

| | | | |
|---|---|---|---|
| 4,564,593 A | 1/1986 | Tsukamoto et al. | |
| 6,228,643 B1 | 5/2001 | Greenland et al. | |
| 6,875,857 B2 * | 4/2005 | Simms | 536/25.4 |
| 2004/0091923 A1 * | 5/2004 | Reyes et al. | 435/6 |
| 2008/0003575 A1 | 1/2008 | Michalak et al. | |
| 2008/0009009 A1 | 1/2008 | Mitsuhashi | |

FOREIGN PATENT DOCUMENTS

WO   WO 91/02740 A1   3/1991

OTHER PUBLICATIONS

Moelling, K. et al., Journal of Virology, "Inhibition of Human Immunodeficiency Virus Type 1 RNase H by Sulfated Polyanions", Dec. 1989, vol. 63, No. 12, pp. 5489-5491.*
Medilexicon.com, "Heparin Unit", also available at http://www.medilexicon.com/medicaldictionary.php?s=heparin+unit; last viewed Aug. 17, 2011.*
Stull, D. et al., The Scientist, "Purely RNA: New innovations enhance the quality, speed, and efficiency of RNA isolation techniques", Nov. 2001, vol. 15, No. 22, pp. 29-31.*
Gopalakrishna et al., Nucleic Acids Research, "Single Step Prokaryotic RNA Isolation", 1981, vol. 9, No. 14, pp. 3545-3554.*
Supplementary European Search Report for European Application No. EP 09763494, dated Mar. 2, 2012, 4 pages.

* cited by examiner

*Primary Examiner* — Shaojia Anna Jiang
*Assistant Examiner* — Bahar Craigo
(74) *Attorney, Agent, or Firm* — Kilpatrick Townsend & Stockton LLP.; M. Henry Heines

(57) ABSTRACT

RNA is extracted from cellular material with a reagent that includes heparin, a reducing agent to reduce disulfide bonds, a chelating agent, a buffer, and an alkali metal halide. The reagent does not require the use of organic solvents, and the reagent allows extraction to be performed in a relatively short period of time in comparison to the prior art.

19 Claims, No Drawings

CELL LYSIS REAGENT FOR ISOLATION OF RNA

CROSS-REFERENCE TO RELATED APPLICATION

This application claims the benefit of U.S. States Provisional Patent Application No. 61/061,159, filed Jun. 13, 2008, the contents of which are incorporated herein by reference.

BACKGROUND OF THE INVENTION

1. Field of the Invention

This invention resides in the field of extracting RNA from eukaryotic cells.

2. Description of the Prior Art

The extraction of RNA from cellular material is an important step in a variety of laboratory procedures for diagnostics, therapy, and research. Extraction is typically achieved by use of an extraction reagent, and to be effective for this purpose, the reagent should extract the RNA, preferably by cell lysis, without disrupting the cell nuclei. An effective reagent should also inhibit any enzymes in the material that degrade RNA, such as RNAses, so that the RNA remains intact both during and after extraction. Further, the reagent should disrupt RNA-binding proteins to cause the proteins to release the RNA and to make the proteins incapable of further binding, even when the proteins are still in contact with the RNA. Still further, the reagent should disrupt any secondary or tertiary RNA structures, for example by chelation, so that the RNA can be used in subsequent processes and reactions.

U.S. Pat. No. 6,875,857 of Simms ("Reagent for the Isolation of RNA," issued Apr. 5, 2005) describes a reagent for extraction of RNA from cellular material, particularly plant cells, that includes one or more nonionic detergents such as tergitol (tert.-octylphenoxy poly(oxyethylene)ethanol), one or more ionic detergents such as sodium dodecylbenzenesulfonate (SDS), one or more chelators such as EDTA, one or more reducing agents such as beta-mercaptoethanol, and one or more antibacterial agents such as sodium azide. While such a reagent appears to be effective for extracting RNA from plant cells and "other difficult materials," according to the patent, the reagent is a harsh reagent and, in addition, requires the subsequent use of an organic solvent such as chloroform to purify the RNA. Chloroform is a toxic material; and the use of chlorinated solvents in general are disfavored due to environmental considerations.

Other procedures in the prior art for isolating RNA from cellular material include those that utilize phenol, chloroform or isoamyl alcohol for extraction, as well as procedures that include the use of a chaotropic agent such as GITC (guanidine isothiocyanate) to precipitate nucleic acids. All of these procedures entail multiple steps, the use of hazardous chemicals, or both, and can take several hours to perform. One such procedure is disclosed in United States Pre-Grant Patent Application Publication No. US 2007/0015165 A1 of Chen et al. (publication date Jan. 18, 2007). Reagents for RNA extraction that have been commercially available include reagents bearing the product name AURUM™, of Bio-Rad Laboratories, Inc., of Hercules, Calif., USA. The AURUM products contain GITC-type compounds. Another commercial reagent for RNA extraction is CytosAll™ (a product of Thermo Fisher Scientific, Inc., Waltham, Mass., USA), which requires the addition of a protein-based RNAse inhibitor.

SUMMARY OF THE INVENTION

It has now been discovered that RNA can be extracted to a high degree of efficiency from cellular material by use of a reagent that contains heparin, a reducing agent to reduce disulfide bonds, a chelating agent, a buffer, and an alkali metal halide. A nonionic detergent can be included as a further but optional component. The efficiency in the use of this reagent arises from the fact that it does not require the use of organic solvents, and it can be performed in a relatively short period of time in comparison to the prior art. In addition, the reagent is not chemically or physically harsh on the cellular material or to the user or the environment. The invention resides in the reagent itself as well as in the use of the reagent for the extraction of RNA from cellular material.

DETAILED DESCRIPTION OF THE INVENTION AND PREFERRED EMBODIMENTS

The heparin content of the reagent of the present invention is from about 1 pg/µL to about 10 pg/µL of the reagent, preferably from about 1 pg/µL to about 5 pg/µL, and most preferably from about 1 pg/µL to about 3 pg/µL. Various forms of heparin, including heparin salts, can be used. The heparin stock used in preparing the reagent is preferably 98% or greater in purity.

The reducing agent included in the reagent can be any reducing agent that is known to reduce disulfide bonds in cellular proteins. Examples of such reducing agents are mercaptans, and preferred mercaptans are dithiothreitol, β-mercaptoethanol, and tris(2-carboxyethyl)phosphine (TCEP). Dithiothreitol and β-mercaptoethanol are particularly preferred. The concentration of reducing agent in the reagent in accordance with this invention is from about 1 mM to about 10 mM, preferably from about 1 mM to about 5 mM.

The chelating agent is included in any amount that will disrupt secondary and tertiary structures of RNA. In most cases, best results will be obtained with a chelating agent in a concentration ranging from about 0.3 mM to about 3 mM, and preferably about 1 mM. Examples of suitable chelating agents are ethylenediaminetetraacetic acid, ethylene glycol tetraacetic acid, citric acid, salicylic acid, salts of ethylenediaminetetraacetic acid, ethylene glycol tetraacetic acid, citric acid, and salicylic acid, as well as phthalic acids, histidines, histidinol dihydrochlorides, and 8-hydroxyquinoline. Ethylenediaminetetraacetic acid (EDTA) is preferred.

The buffer is preferably one that maintains the pH of the reagent relatively close to physiological conditions, or from about 7.5 to about 8.0. Examples of suitable buffers are tris (hydroxymethyl)aminomethane (Tris base), tris(hydroxymethyl)aminomethane hydrochloride (Tris-HCl), bis(2-hydroxyethyl)iminotris-(hydroxymethyl)methane (Bis-Tris base), bis(2-hydroxyethyl)iminotris-(hydroxymethyl)methane hydrochloride (Bis-Tris-HCl), and N-2-hydroxyethyl-piperazine-N-2-ethanesulfonic acid (HEPES). The concentration of the buffer will vary with the actual buffer used, but in most cases, best results will be achieved with a buffer in a concentration of from about 1 mM to about 100 mM, preferably from about 10 mM to about 50 mM.

The alkali metal halide is included to maintain ionic strength. Alkali metal chlorides are preferred, particularly sodium, potassium or lithium chloride, which may be used individually or in mixtures of two or all three. For best results, the concentration of the alkali metal halide will range from about 1 mM to about 100 mM, preferably from about 10 mM to about 50 mM.

The reagent optionally contains one or more nonionic surfactants or detergents, for example, alkylphenoxy poly(oxyethylene)alkanols such as NP-40 or tergitol (IGEPAL®). Tergitols are generally tert.-octylphenoxy poly(oxyethylene) ethanols. Other suitable poly(oxyethylene)alkanols are TRITON® products (octylphenol polyethoxylates) and TWEEN® products (polyoxyethylene derivatives of various fatty acids). If present in the reagent, the nonionic detergent is preferably included in an amount of up to 2.5%, more preferably from about 0.5% to about 2.5%, and most preferably from about 0.5% to about 2%, by volume.

The cellular material from which the reagents of this invention can be used effectively to extract RNA include any individual biological cells that contain RNA, and any tissue or other cell masses that include such cells. RNA can thus be extracted from animal cellular material, including mammalian cellular material, by this invention.

The reagents of this invention do not require the ionic (cationic or anionic) detergents cited in the Simms patent referenced above as "secondary" or "helper" detergents, and preferred reagent compositions in accordance with this invention do not contain these detergents. By avoiding these detergents, the reagent can extract RNA from cellular material under conditions that are more gentle than those that exist when these detergents are present. The reagents of this invention are also effective without the use of an organic solvent for extraction of the supernatant. Such use of an organic solvent, notably chloroform, is cited in the Simms patent referenced above. Furthermore, the reagents of this invention do not require the use of a chaotrope or of silica binding. Without these additional reagents or procedural steps, an extraction process using a reagent of this invention can be performed in relatively few steps and can be complete in only about ten minutes.

EXAMPLES

The following general procedure is used to extract RNA from a cellular material with reagents of this invention:

The chosen cells are washed with PBS solution (50 mM potassium phosphate and 150 mM NaCl; pH 7.2) with spinning (500 rcf at 4° C.) and are resuspended in PBS to the desired concentration (1-1000 cells/µL as the dynamic range for lysis). The cells are then pelletized and the PBS solution removed and replaced with an equal volume of an RNA extraction reagent according to the invention, by adding the reagent directly to the pelletized cells. The resulting mixture is vortexed for about 30 seconds, then spun for 3 minutes at 5000 rcf at room temperature to pelletize the cell nuclei. The supernatant liquid, which contains the extracted RNA, is then removed and is ready for downstream use without further extraction or processing.

Reagents in accordance with this invention were assessed by their ability to lyse cells efficiently within the range of 1-1000 cells/µL. Success was measured by evaluating the linearity of the standard curve with respect to cell concentrations across three logs using quantitative RT-PCR. The presence of genomic DNA in the lysate was also evaluated. There had to be at least 25-fold less genomic DNA for a given gene than its mRNA, as measured by quantitative RT-PCR, for the formulation to be considered successful.

Tables 1, 2, and 3 below show compositions of reagent solutions according to the invention that were tested in extracting RNA from HeLa cells, and deemed successful by the above standards. The solutions contained heparin, EDTA, and dithiothreitol (DTT) in the indicated amounts, and other ingredients as specified.

TABLE 1

Reagents That Successfully Extracted RNA from HeLa Cells

| Reagent No. | pH  | EDTA, mM | DTT, mM | Heparin, pg/µL |
|---|---|---|---|---|
| 1 | 7.5 | 1 | 1 | 1 |
| 2 | 7.5 | 1 | 1 | 5 |
| 3 | 7.5 | 1 | 1 | 10 |
| 4 | 7.5 | 1 | 5 | 1 |
| 5 | 7.5 | 1 | 5 | 5 |
| 6 | 7.5 | 1 | 5 | 10 |
| 7 | 7.5 | 1 | 10 | 1 |
| 8 | 7.5 | 1 | 10 | 5 |
| 9 | 7.5 | 1 | 10 | 10 |

Type 1: EDTA, DTT, and Heparin in Amounts shown, plus 10 mM Tris, pH 7.5; 10 mM NaCl; 1.25 v/v % NP-40 detergent

TABLE 2

Reagents That Successfully Extracted RNA from HeLa Cells

| Reagent No. | pH  | EDTA, mM | DTT, mM | Heparin, pg/µL |
|---|---|---|---|---|
| 10 | 8.0 | 1 | 1 | 10 |
| 11 | 8.0 | 1 | 5 | 1 |
| 12 | 8.0 | 1 | 5 | 5 |
| 13 | 8.0 | 1 | 5 | 10 |
| 14 | 8.0 | 1 | 10 | 1 |
| 15 | 8.0 | 1 | 10 | 5 |
| 16 | 8.0 | 1 | 10 | 10 |
| 17 | 8.0 | 1 | 1 | 0 |
| 18 | 8.0 | 1 | 1 | 1 |

Type 2: EDTA, DTT, and Heparin in Amounts shown, plus 10 mM Tris, pH 8.0; 10 mM NaCl; 1.25 v/v % NP-40 detergent

TABLE 3

Reagents That Successfully Extracted RNA from HeLa Cells

| Reagent No. | pH  | EDTA, mM | DTT, mM | Heparin, pg/µL |
|---|---|---|---|---|
| 19 | 8.0 | 1 | 1 | 0 |
| 20 | 8.0 | 1 | 1 | 1 |
| 21 | 8.0 | 1 | 1 | 5 |
| 22 | 8.0 | 1 | 1 | 10 |
| 23 | 8.0 | 1 | 5 | 1 |
| 24 | 8.0 | 1 | 5 | 5 |
| 25 | 8.0 | 1 | 5 | 10 |
| 26 | 8.0 | 1 | 10 | 1 |
| 27 | 8.0 | 1 | 10 | 5 |
| 28 | 8.0 | 1 | 10 | 10 |

Type 3: EDTA, DTT, and Heparin in Amounts shown, plus 10 mM Tris, pH 8.0; 50 mM NaCl; 1.25 v/v % NP-40 detergent In the claim or claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A reagent for extracting RNA from cellular material, said reagent comprising:
(a) from about 1 pg/µL to about 10 pg/µL heparin;

(b) from about 1 mM to about 10 mM of a reducing agent effective to reduce disulfide bonds in cellular proteins;

(c) a chelating agent in an amount sufficient to disrupt RNA secondary and tertiary structures;

(d) from about 1 mM to about 100 mM of a buffer selected from the group consisting of Tris base, Tris-HCl, Bis-Tris base, Bis-Tris-HCl, and HEPES; and (e) from about 1 mM to about 100 mM of an alkali metal halide;

said reagent being devoid of chlorinated solvents.

2. The reagent of claim 1 wherein said heparin constitutes from about 1 pg/µL to about 3 pg/µL of said reagent.

3. The reagent of claim 1 wherein said reducing agent constitutes from about 1 mM to about 5 mM of said reagent.

4. The reagent of claim 1 wherein said reducing agent is a member selected from the group consisting of dithiothreitol, β-mercaptoethanol and tris(2-carboxyethyl)phosphine.

5. The reagent of claim 1 wherein said chelating agent is a member selected from the group consisting of ethylenediaminetetraacetic acid; ethylene glycol tetraacetic acid; citric acid; salicylic acid; salts of ethylenediaminetetraacetic acid, ethylene glycol tetraacetic acid, citric acid, and salicylic acid; a phthalic acid; a histidine; a histidinol dihydrochloride; and 8-hydroxyquinoline.

6. The reagent of claim 1 wherein said chelating agent is ethylenediaminetetraacetic acid.

7. The reagent of claim 1 wherein said chelating agent constitutes from about 0.3 mM to about 3 mM of said reagent.

8. The reagent of claim 1 wherein said buffer constitutes an amount of said reagent that maintains the pH of said reagent at from about 7.5 to about 8.0.

9. The reagent of claim 1 wherein said alkali metal halide is selected from the group consisting of sodium chloride, potassium chloride, and lithium chloride.

10. The reagent of claim 1 wherein said alkali metal halide is an alkali metal chloride and constitutes from about 10 mM to about 50 mM of said reagent.

11. The reagent of claim 1 further comprising a nonionic detergent in an amount less than or equal to about 2.5% by volume.

12. The reagent of claim 1 wherein said reagent is devoid of cationic detergents and anionic detergents.

13. The reagent of claim 1 wherein said reagent is devoid of organic solvents.

14. A method for extracting RNA from cellular material, said method comprising contacting said cellular material with the reagent of claim 1 to a degree sufficient to extract said RNA into a supernatant, and recovering said supernatant from the remainder of said cellular material.

15. The method of claim 14 performed without extracting said supernatant with an organic solvent.

16. The method of claim 14 performed without treatment of said cellular material with an enzyme to remove genomic DNA therefrom.

17. The method of claim 14 performed without heating of said cellular material to denature proteins therein.

18. The method of claim 14 wherein said heparin constitutes from about 1 pg/mL to about 3 pg/mL of said reagent, said reducing agent constitutes from about 1 mM to about 5 mM of said reagent, said chelating agent is ethylenediaminetetraacetic acid and constitutes from about 0.3 mM to about 3 mM of said reagent, said buffer constitutes an amount of said reagent that maintains the pH of said reagent at from about 7.5 to about 8.0, and said alkali metal halide constitutes from about 10 mM to about 50 mM of said reagent.

19. The method of claim 14 wherein said reagent further comprises a nonionic detergent in an amount less than or equal to about 2.5% by volume and is devoid of ionic detergents.

* * * * *